United States Patent
Ohga et al.

(10) Patent No.: US 9,291,633 B2
(45) Date of Patent: Mar. 22, 2016

(54) AUTOMATED SAMPLE PROCESSING SYSTEM

(75) Inventors: Hiroshi Ohga, Hitachiomiya (JP);
Tatsuya Fukugaki, Hitachinaka (JP);
Tetsuya Isobe, Hitachinaka (JP);
Shigeru Yano, Hitachinaka (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 588 days.

(21) Appl. No.: 13/383,508

(22) PCT Filed: Sep. 9, 2010

(86) PCT No.: PCT/JP2010/065537
§ 371 (c)(1),
(2), (4) Date: Jan. 27, 2012

(87) PCT Pub. No.: WO2011/040203
PCT Pub. Date: Apr. 7, 2011

(65) Prior Publication Data
US 2012/0174687 A1    Jul. 12, 2012

(30) Foreign Application Priority Data
Sep. 30, 2009 (JP) ................................. 2009-225943

(51) Int. Cl.
*G01N 1/10* (2006.01)
*G01N 35/02* (2006.01)
*G01N 35/00* (2006.01)
*G01N 35/04* (2006.01)

(52) U.S. Cl.
CPC .......... *G01N 35/026* (2013.01); *G01N 35/0095* (2013.01); *G01N 2035/00326* (2013.01); *G01N 2035/0415* (2013.01)

(58) Field of Classification Search
None
See application file for complete search history.

(56) References Cited

U.S. PATENT DOCUMENTS

| | | | |
|---|---|---|---|
| 6,290,907 B1 * | 9/2001 | Takahashi et al. | 422/65 |
| 6,444,171 B1 * | 9/2002 | Sakazume et al. | 422/65 |
| 2002/0028157 A1 * | 3/2002 | Takahashi et al. | 422/65 |
| 2004/0208787 A1 * | 10/2004 | Takahashi et al. | 422/64 |
| 2005/0036913 A1 * | 2/2005 | Yamakawa et al. | 422/65 |
| 2005/0070019 A1 * | 3/2005 | Yamamoto | 436/43 |
| 2008/0050279 A1 * | 2/2008 | Fujita | 422/67 |
| 2008/0069730 A1 * | 3/2008 | Itoh | 422/65 |

(Continued)

FOREIGN PATENT DOCUMENTS

JP    09-274046    10/1997
JP    10-090277    4/1998

(Continued)

*Primary Examiner* — Jill Warden
*Assistant Examiner* — Benjamin Whatley
(74) *Attorney, Agent, or Firm* — Mattingly & Malur, PC

(57) ABSTRACT

After being dispensed, a sample that needs to be quickly measured passes through another unit and is transported to an automatic analyzer. A plurality of units are provided for functions of processing including a dispensing unit that dispenses the sample stored in a sample vessel into another sample vessel. At least one discharge line discharges the sample from the dispensing unit to a transport line and a line that is perpendicular to the discharge line. A reverse direction transport line transports the sample in a direction reverse to a direction in which the sample loaded in the system is transported to the dispensing unit. The sample that is processed by the dispensing unit is transported to a storage unit located on the upstream side of the system, through the reverse direction transport line.

5 Claims, 6 Drawing Sheets

(56) References Cited

U.S. PATENT DOCUMENTS

2009/0191095 A1* 7/2009 Nakamura .................. 422/67
2012/0266698 A1* 10/2012 Isobe et al. ................ 73/863.92

FOREIGN PATENT DOCUMENTS

| JP | 11-083865 | 3/1999 |
|---|---|---|
| JP | 11-304811 | 5/1999 |
| JP | 2004-061169 | 2/2004 |
| JP | 2007-057332 | 3/2007 |
| JP | 2007057332 A * | 3/2007 |
| JP | 2008-076185 | 4/2008 |
| JP | 2009-008558 | 1/2009 |
| JP | 2009008558 A * | 1/2009 |
| JP | 2009-180607 | 8/2009 |
| JP | 2010-091434 | 4/2010 |

* cited by examiner

FIG. 6
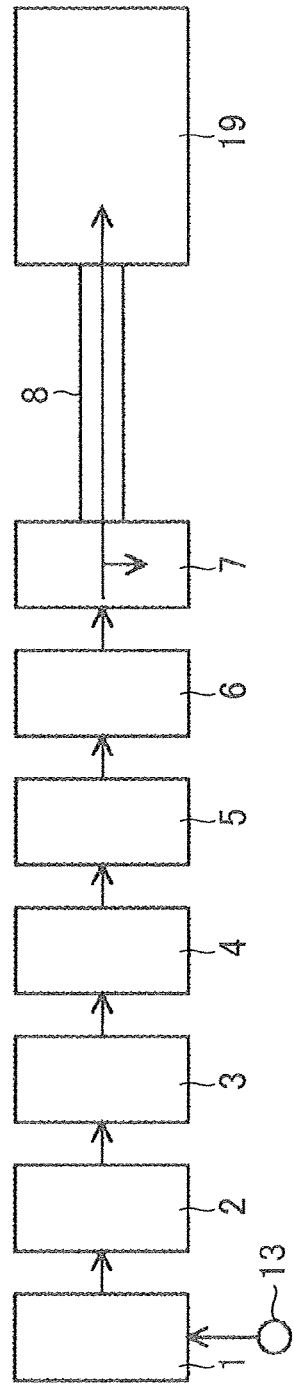
FLOW OF PROCESS TO BE PERFORMED
ON SAMPLE BY CONVENTIONAL SYSTEM
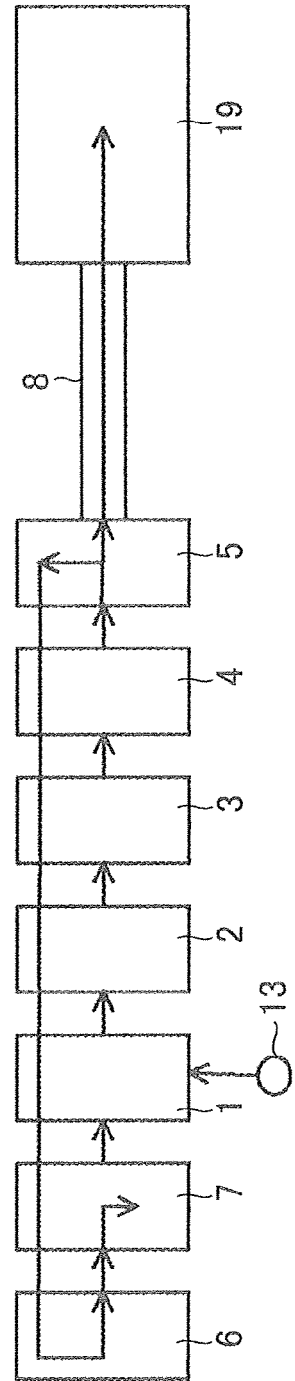
EXAMPLE OF FLOW OF PROCESS TO BE PERFORMED ON SAMPLE
BY SYSTEM ACCORDING TO THE PRESENT INVENTION

AUTOMATED SAMPLE PROCESSING SYSTEM

TECHNICAL FIELD

The present invention relates to an automated sample processing system that automatically processes a sample.

BACKGROUND ART

A conventional automated sample processing system includes units having various types of functions located between a loading unit and a storage unit as described in Patent Document 1. Typically, the conventional automated sample processing system has a structure in which a sample is loaded from the loading unit located on the upstream side of the system for processing the sample and is processed by the various units so that the processed sample is stored in the storage unit located on the most downstream side. In order to transport the sample to a location at which the next process is performed, the sample then passes through a discharge line of the storage unit. Then, the sample is transported to the location at which the next process such as a process of automatically analyzing the sample is performed.

The aforementioned configuration is effective when the sample is processed while being transported in one direction. Similarly to the aforementioned system, in another automated sample processing system configured such that a loading unit, a centrifuge unit, an opening unit, a storage unit and the like are fixed without the units being combined, a dispensing device is not located on the most downstream side of the system for processing a sample.

In addition, as described with reference to FIG. 1 of Patent Document 2, a sample is supplied from a sample supply unit, passes through a dispensing unit and a vessel supply unit, and is transported to a sample discharge unit.

In a system that is designed on the premise that a sample is subjected to pretreatments, the pretreatments to be performed by an operator on a sample, that is, a series of operations are automated such as an arrival confirmation of the sample, centrifugal separation to be performed on the sample, opening of a plug of a sample vessel, dispensing of a serum of the sample into another vessel, closing of the vessel into which the sample has been dispensed, and storage of the processed sample.

Thus, the dispensing operation is performed during the pretreatments and is not performed on the most downstream side of the system for processing the sample.

In recent years, sample processing is strongly required to be performed automatically. For that purpose, there is an automated system in which a stored sample is automatically retrieved from a storage unit in order to reinspect the sample and transported through an automatic transport line to an automatic analyzer.

PRIOR ART LITERATURE

Patent Document

Patent Document 1: JP-11-304811-A
Patent Document 2: JP-2010-914341-A

SUMMARY OF THE INVENTION

Problem to be Solved by the Invention

A sample that is dispensed from a vessel into another vessel by a dispensing unit is transported to an automatic analyzer so that a component of the sample is measured. Since the measured component of the sample is treated as an index for a treatment, the shorter a time period elapsing from the time when the sample is collected to the time when a result of the measurement of the component is output, the better.

However, in the conventional automated sample processing systems, processing units such as a storage unit and a vessel closing unit are located at positions on the downstream side of the system relative to the position where the process by the dispensing unit is performed. Thus, in each of the conventional automated sample processing systems, a sample is transported to a transport line after it passes through an unnecessary unit and is then transported to an automatic analyzer. In addition, as the capacity of each of the storage units is limited, if the storage unit is beyond the storing capacity thereof, the transport and discharge of the sample will be stopped. The transport and discharge of the sample will be continuously stopped until an operator removes the sample from the storage unit. Thus, the transport of the sample to the automatic analyzer is disadvantageously delayed.

For a conventional automated sample processing system illustrated in FIG. 7, when a sample that is stored in a storage unit needs to be reinspected, the sample that is transported from the storage unit merges with another sample that has been loaded from a sample loading unit and is transported toward the upstream side, on a transport line. Thus, the transport line may be congested.

An object of the present invention is to provide an automated sample processing system that transports a dispensed sample to an automatic analyzer for the shortest time period.

Means for Solving the Problem

In order to accomplish the aforementioned object, features of a configuration of the present invention are as follows. A dispensing unit that dispenses a sample stored in a vessel into another vessel includes: a discharge line that discharges the original sample or the vessel storing the dispensed sample to a transport line for transporting the original sample or the vessel to an automatic analyzer; a line that is located in the dispensing unit and perpendicular to the discharge line; a dispensing unit; a reverse direction transport line that transports, in a upstream direction, the sample that has been processed by the dispensing unit and is to be stored, the upstream direction being reverse to a direction in which the sample from a loading unit is transported to the dispensing unit.

The dispensing unit may further include: a mechanism that is capable of simultaneously stopping one or more samples on the transport lines and in front of an intersection of the transport lines located in the dispensing unit and is capable of discharging the samples on a sample basis; a device that reads an identification number or sign of the vessel storing the sample; a stopper that is constituted by a mechanism for stopping or transporting the sample on or through the lines; a function of enabling the reading device to communicate with a computer located in the dispensing unit or a computer located outside the dispensing unit and connected to the computer located in the dispensing unit; and a function of opening and closing the stopper in accordance with an instruction provided by the computer and controlling a destination of the sample.

Effect of the Invention

According to the present invention, the dispensing unit is arranged on the most downstream side of a range in which the sample is processed. Thus, a time period during which the dispensed sample is transported to the automatic analyzer can be reduced, while the dispensed sample does not pass through or stay in another unit.

A discharge section is provided for each type of vessels that hold samples. Thus, a time period during which a sample is transported to the automatic analyzer can be reduced. In addition, a device for placing the sample in another vessel is not necessary. Thus, the system that can transport the sample in a short period of time can be configured with a low cost.

In addition, a loading unit and a storage unit accessed by an operator for the automatic sample processing system can be arranged adjacent to each other so that a work range of the operator is small and efficient work can be provided.

BRIEF DESCRIPTION OF THE DRAWINGS

FIG. 6 is a flowchart of a process to be performed by a conventional system and a flowchart of a process to be performed by the system according to the present invention.

MODE FOR CARRYING OUT THE INVENTION

Embodiments of the present invention are described below with reference to the accompanying drawings.

Figure 1:
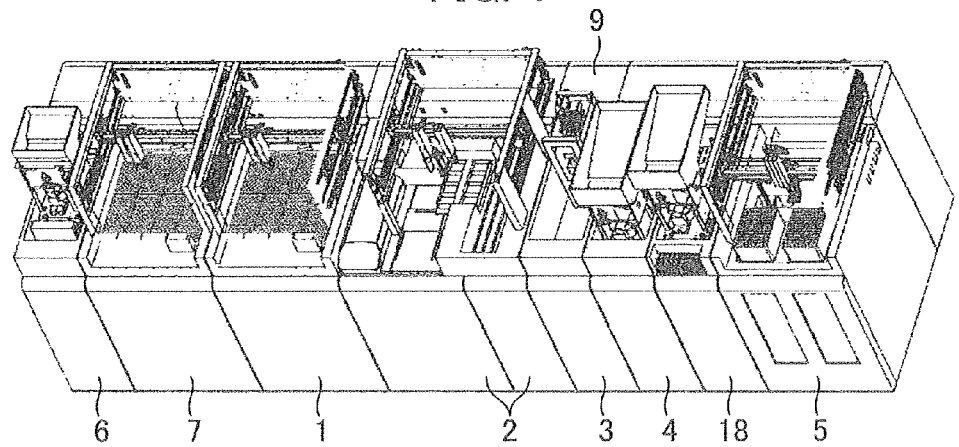
FIG. 1 is a diagram illustrating a system according to a first embodiment of the present invention.
Figure 2:
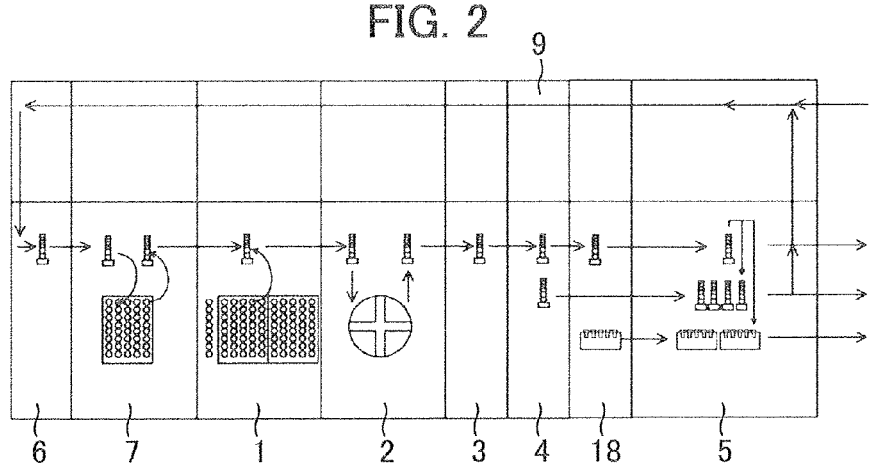
FIG. 2 is a block diagram illustrating the first embodiment of the present invention.
Figure 3:
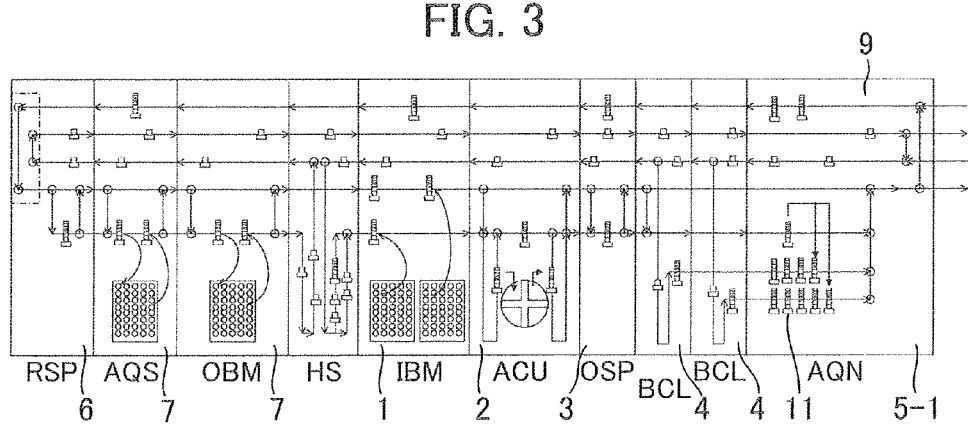
FIG. 3 is a block diagram illustrating a modified example of the block diagram of FIG. 2.
Figure 4:
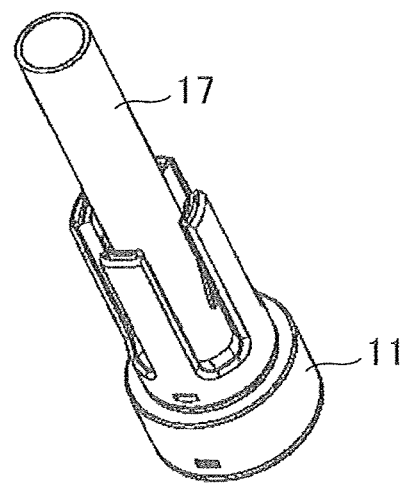
FIG. 4 is a diagram illustrating a single-sample holder.
Figure 5:
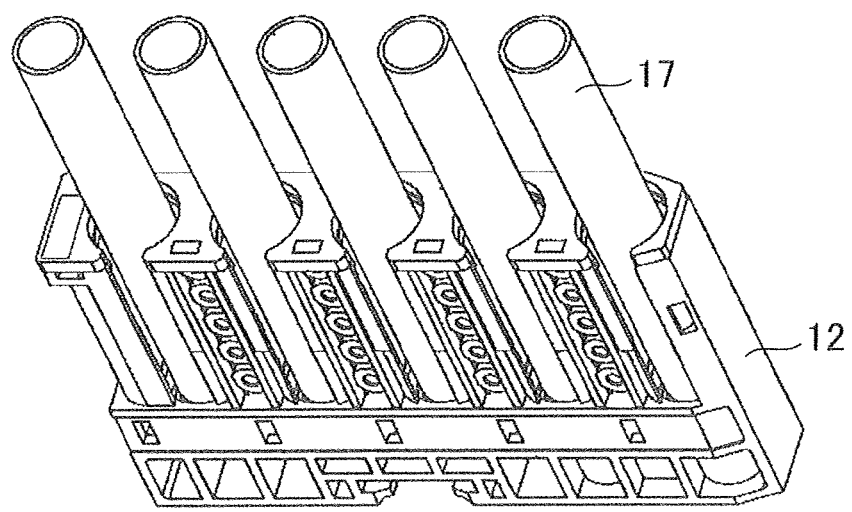
FIG. 5 is a diagram illustrating a multi-sample rack.

FIG. 1 is a diagram illustrating one of examples of a system configuration of an automated sample processing system according to an embodiment of the present invention. FIG. 2 is a block diagram illustrating the flow of a process that is performed on a sample in the system configuration illustrated in FIG. 1. FIG. 3 is a diagram illustrating a usage example of the block diagram illustrated in FIG. 2 and illustrates a modified example of a dispensing unit 5 illustrated in FIG. 2. FIGS. 4 and 5 are diagrams illustrating parts for holding and transporting a sample in the system. FIG. 4 illustrates an example of a single-sample holder for holding and transporting a single sample. FIG. 5 illustrates an example of a rack capable of holding five samples.

In FIG. 1, reference numeral 1 denotes a loading unit. A sample is normally loaded from the loading unit 1. Reference numeral 2 denotes an automatic centrifuge unit. The automatic centrifuge unit 2 automatically places the sample in a rotor located in a centrifuge, automatically performs centrifugal separation on the sample, and automatically discharges the sample. Reference numeral 3 denotes an automatic opening unit that automatically pulls out a plug. Reference numeral 4 denotes an automatic barcode attaching unit that automatically attaches a barcode label to a vessel such as a test tube. Reference numeral 18 denotes a vessel and rack supply unit that automatically places the vessel at the rack denoted by reference numeral 12 and discharges the rack holding the vessel. Reference numeral 5 denotes the dispensing unit that dispenses the sample (hereinafter referred to as primary sample) subjected to the centrifugal separation into another vessel. In order to distinguish the primary sample from the sample dispensed into the vessel, the dispensed sample is hereinafter referred to as a secondary sample. In an example illustrated in FIG. 2, directions indicated by arrows means directions in which the primary sample and the secondary sample are transported. In the example illustrated in FIG. 2, the dispensing unit 5 dispenses the primary sample so as to generate a plurality of secondary samples. In this case, the secondary samples are generated in order for the secondary samples to be analyzed by an automatic analyzer and are transported from the dispensing unit 5 directly to a transport line connected with the automated analyzer without passing through another unit. The secondary samples are then transported to the automatic analyzer. The primary sample is transported by a reverse transport line 9 that is arranged in the automated sample processing system. The vessel holding the sample is attached with a plug by a closing unit 6 and then, stored in a storage unit 7. Another line is provided, which is perpendicular to the transport line that transports a processed primary sample 13 or secondary samples 14. Further, the reverse transport line 9 is arranged in the automatic sample processing system so that a sample is transported to the automatic analyzer for the shortest time period without passing through another unit. FIG. 3 illustrates an example in which a secondary sample that is dispensed by the dispensing unit 5 illustrated in FIG. 2 is generated in a single holder 11.

FIG. 6 is a diagram illustrating an example of the flow of a process that is performed by a conventional automated sample processing system.

The sample 13 is loaded from a loading unit 1 located on the most upstream side of the system and is processed in order as illustrated in FIG. 6, thus a secondary sample is generated by a dispensing unit 5.

In this case, the primary sample and the secondary sample are transported through the same transport line, with the primary sample attached with a plug on its vessel by an automatic closing unit 6 to be transported to a storage unit 7 while the secondary sample is transported to an automatic analyzer 19 through a transport line 8. In the configuration of the conventional system, a time period T during which the secondary sample to be measured by the automatic analyzer is transported after the process performed by the dispensing unit 5 is equal to the sum of a time period for a closing process to be performed by the automatic closing unit 6, a time period for waiting for a process of storing the primary sample in the storage unit 7, and a time period for a process of the transport through the transport line 8.

In the flow of a process to be performed by the automatic sample processing system according to the embodiment of the present invention, after discharged from the dispensing unit 5, the secondary samples that have been processed by the dispensing unit 5 to be measured by the automatic analyzer can be immediately transported to the automatic analyzer 19 through the transport line 8. A time period T during which the secondary samples to be measured by the automatic analyzer in the automated sample processing system according to the present invention are transported after the process performed by the dispensing unit 5, is equal to a time period for the process of the transport through the transport line 8. Thus, the samples can be transported to the automatic analyzer for a shorter time and start to be measured.

When an operator needs to load the sample and remove the stored sample, in the conventional automated sample processing system illustrated in FIG. 6, the operator needs to move back and forth between the loading unit 1 located on the leftmost side in FIG. 6 and the storage unit 7. In the arrangement according to the present invention, however, as the sample loading unit 1 and the storage unit 7 are located adjacent to each other, the operator can load the sample and remove the stored sample in a small work range.

Figure 7:
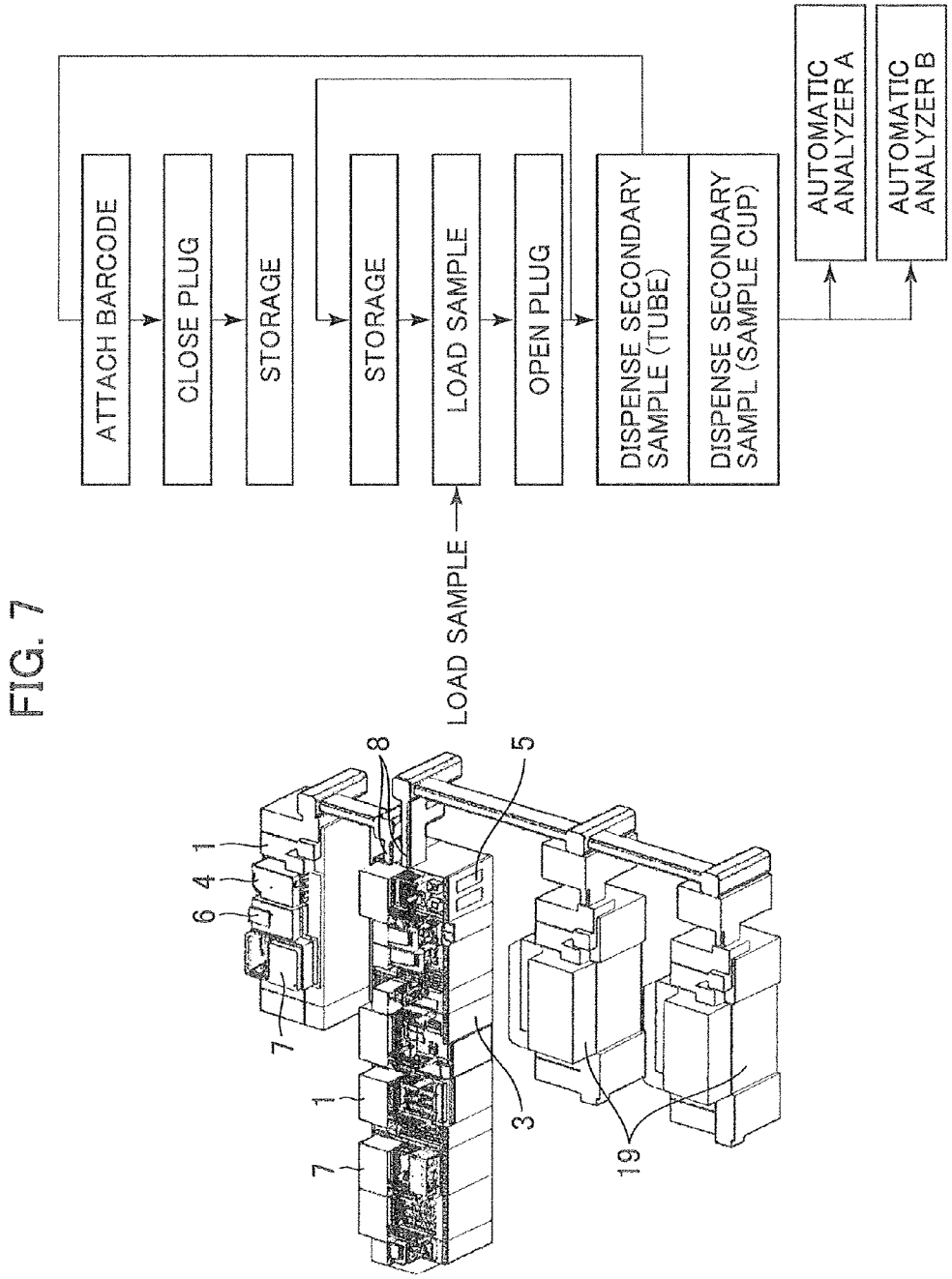
FIG. 7 is a block diagram and a diagram illustrating a system according to a second embodiment of the present invention.

FIG. 7 illustrates the configuration of a system according to a second embodiment of the present invention and a flowchart of a process that is performed by the system. The dispensing unit 5 is characterized in that it has discharge ports different in shape from each other. One of the discharge ports is provided for the single holder 11, while the other is for the sample rack 12. Since the dispensing unit 5 has the plurality of discharge ports, the sample rack that holds a vessel that is called a sample cup for a secondary sample is transported to the automatic analyzer without passing through another unit and the other secondary sample can be transported to another automated sample processing system through another path.

Figure 8:
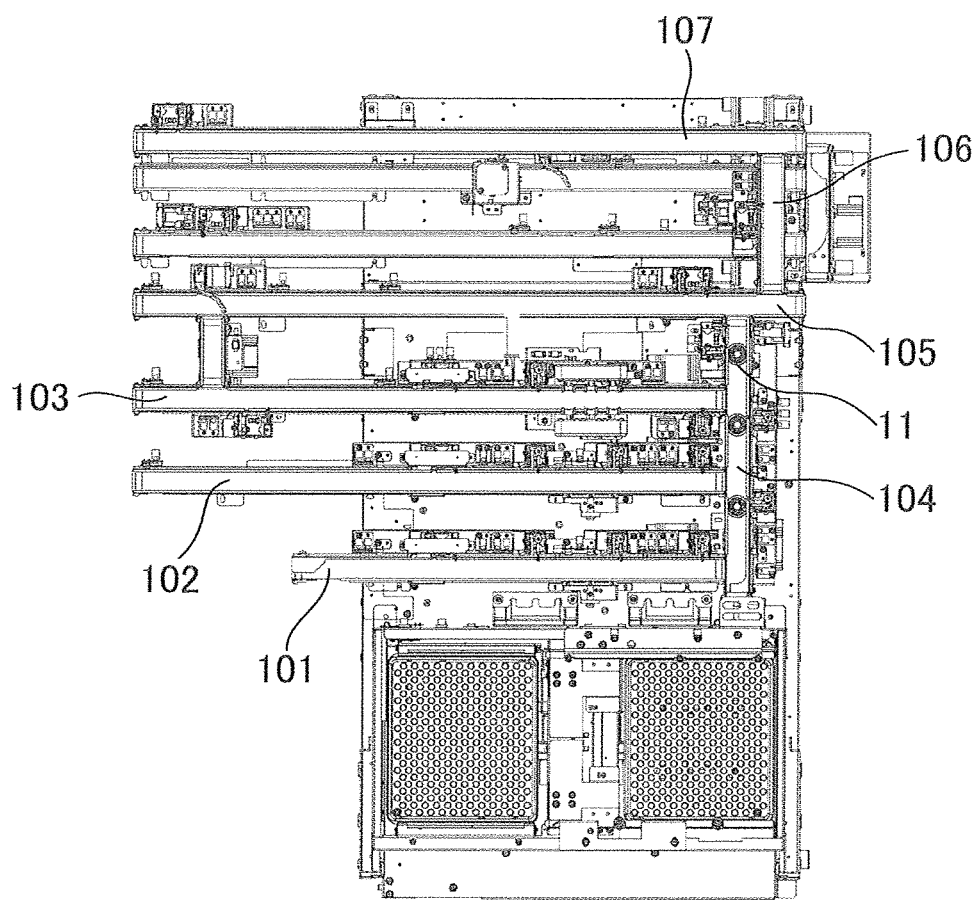
FIG. 8 is a detailed plan view of internal transport lines of a dispensing unit.
Figure 9:
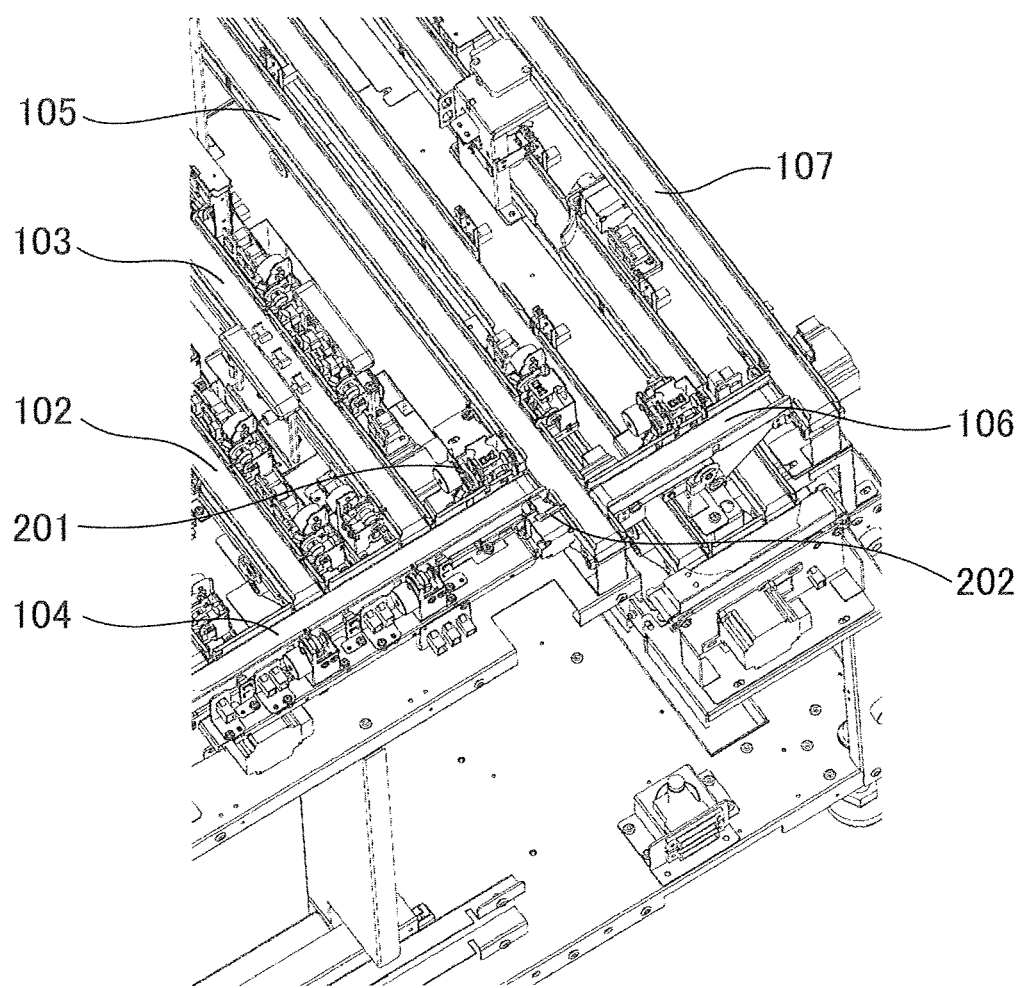
FIG. 9 is a perspective view of a part of the internal transport lines illustrated in FIG. 8.

FIG. 8 is a detailed plan view of internal transport lines of the dispensing unit 5. FIG. 9 is a perspective view of a part of the internal transport lines illustrated in FIG. 8. The primary sample 13 is transported by a primary sample line 103 and dispensed at a predetermined position so that the secondary samples 14 are generated. In the present embodiment, the secondary samples 14 are transported by two lines that are a secondary sample line B 101 and a secondary sample line A 102. The primary sample 13 and the secondary samples 14 pass through a direct line 104 and are temporarily stopped by a stopper 201 at which a contactless ID reading device is installed. The contactless ID reading device reads IDs of the samples and uses communication means to transmit the contents of the IDs to a CPU that is included in the reading device. The CPU included in the reading device receives, from a personal computer or the like placed outside the reading device, information on transport paths of the IDs in advance, and opens and closes a gate 202 in accordance with the information. Specifically, when the primary sample 13 or the secondary sample 14 needs to be transported toward the downstream side, the gate is open and the primary sample 13 or the secondary sample 14 is transported toward the downstream side by a main sample transport line 105. In addition, when the primary sample 13 or the secondary sample 14 needs to be transported toward the upstream side, the gate 202 is closed and the primary sample 13 or the secondary sample 14 is transported to the direct line B, passes therethrough and then, transported to a reverse transport line 107 to be directed to the upstream side by the reverse transport line 107.

DESCRIPTION OF REFERENCE NUMERALS

1 Sample loading unit
2 Automatic centrifuge unit
3 Automatic opening unit
4 Automatic barcode attaching unit
5 Dispensing unit
5-1 Dispensing unit
6 Automatic closing unit
7 Storage unit
8 Transport line
9 Reverse transport line
10 Automatic analyzer connecting transport line
11 Single-sample holder
12 Sample rack
13 Primary sample
14 Secondary sample
15 Control PC
16 Controller
17 Test tube
18 Vessel and rack supply unit
19 Automatic analyzer
101 Secondary sample line B
102 Secondary sample line A
103 Primary sample line
104 Direct line A
105 Main sample transport line
106 Direct line B
107 Reverse transport line
201 Stopper
202 Gate

The invention claimed is:

1. An automated sample processing system comprising:
a plurality of units that are provided for functions of processing a sample and combined so as to form the system,
wherein the combined plurality of units include a dispensing unit,
wherein the dispensing unit dispenses the sample,
wherein the dispensing unit is located on the most downstream side of the combined plurality of units, and
wherein the dispensing unit includes:
a single-sample holder transport line that transports a first single-sample holder which holds a single sample vessel storing the sample;
a multi-sample rack transport line that transports a multi-sample rack which holds a plurality of sample vessels;
a dispensing device that dispenses the sample stored in the single sample vessel held by the first single-sample holder into the plurality of sample vessels held by the multi-sample rack or another single sample vessel held by a second single-sample holder;
a plurality of discharge ports which separately discharge the second single-sample holder and the multi-sample rack from the dispensing unit to an analyzing unit, which is connected downstream of the dispensing unit by a transport line, without passing through other ones of the combined plurality of units, and
a direct line and a reverse transport line, where the direct line transports the first single-sample holder to the reverse transport line to direct the first single-sample holder to an upstream side of the combined plurality of units,
a stopping mechanism for stopping the first single-sample holder, the second single-sample holder and the multi-sample rack prior to the discharge ports, and
a contactless identification (ID) reading device for reading ID information of the sample vessels held by the first single-sample holder, the second single-sample holder and the multi-sample rack stopped by the stopping mechanism.

2. The automated sample processing system according to claim 1, wherein:
the combined plurality of units further include a storage unit that is located on the upstream side of the combined plurality of units and stores the sample stored in the single sample vessel held by the first single-sample holder that has been dispensed or has yet to be dispensed by the dispensing device, and
the reverse transport line directs the first single-sample holder to the storage unit from the dispensing unit.

3. The automated sample processing system according to claim 1, further comprising:
a controller to control the dispensing of the sample stored in the single sample vessel held by the first single-sample holder by the dispensing device.

4. The automated sample processing system according to claim 1, further comprising:

a control unit for determining transport paths of the first single-sample holder, the second single-sample holder and the multi-sample rack based on the ID information, where the transport paths are through the single-sample holder transport line, the multi-sample rack transport line, the direct line, and the reverse transport line.

5. The automated sample processing system according to claim 4, wherein:

the combined plurality of units further include a storing unit to store a plurality of sample vessels located on an upstream side of the combined plurality of units, and the dispensing unit further includes a gating mechanism to sort the sample vessels held by first single-sample holder, the second single-sample holder and the multi-sample rack to the discharge ports or the storing unit based on the ID information read by the contactless ID reading device.

\* \* \* \* \*